(12) United States Patent
German et al.

(10) Patent No.: US 12,338,204 B2
(45) Date of Patent: *Jun. 24, 2025

(54) SUBSTITUTED BISPHENYLALKYLUREA COMPOUNDS AND METHODS OF TREATING BREAST CANCER

(71) Applicant: Texas Tech University System, Lubbock, TX (US)

(72) Inventors: Nadezhda German, Amarillo, TX (US); Ruwein Zhang, Sugar Land, TX (US); Wei Wang, Sugar Land, TX (US); Constantinos Mikelis, Amarillo, TX (US); Luca Cucullo, Amarillo, TX (US)

(73) Assignee: Texas Tech University System, Lubbock, TX (US)

( * ) Notice: Subject to any disclaimer, the term of this patent is extended or adjusted under 35 U.S.C. 154(b) by 811 days.

This patent is subject to a terminal disclaimer.

(21) Appl. No.: 17/267,439

(22) PCT Filed: Aug. 9, 2019

(86) PCT No.: PCT/US2019/046031
§ 371 (c)(1),
(2) Date: Feb. 9, 2021

(87) PCT Pub. No.: WO2020/033909
PCT Pub. Date: Feb. 13, 2020

(65) Prior Publication Data
US 2021/0309607 A1    Oct. 7, 2021

Related U.S. Application Data

(60) Provisional application No. 62/716,933, filed on Aug. 9, 2018.

(51) Int. Cl.
*C07C 275/30*    (2006.01)
*A61K 45/06*    (2006.01)
*A61P 35/00*    (2006.01)

(52) U.S. Cl.
CPC ............ *C07C 275/30* (2013.01); *A61K 45/06* (2013.01); *A61P 35/00* (2018.01)

(58) Field of Classification Search
CPC ........ C07C 275/30; A61K 45/06; A61P 35/00
See application file for complete search history.

(56) References Cited

U.S. PATENT DOCUMENTS

| 11,225,459 B2 * | 1/2022 | German | A61P 25/00 |
| 2008/0125424 A1 * | 5/2008 | DePrez | C07D 417/12 |
| | | | 548/198 |
| 2023/0382850 A1 * | 11/2023 | German | A61P 35/00 |

FOREIGN PATENT DOCUMENTS

| WO | 9741846 A1 | 11/1997 |
| WO | 2008006625 A2 | 1/2008 |

(Continued)

OTHER PUBLICATIONS

Li, W. et al., "Discovery of 1-(-3-aryl-4-chlorophenyl)-3-(p-aryl)urea derivatives against breast cancer by inhibiting PI3K/Akt/mTOR and Hedgehog signalings", European Journal of Medicinal Chemistry, vol. 141, Oct. 6, 2017, 721-733; 14 pages.

(Continued)

*Primary Examiner* — Clinton A Brooks
*Assistant Examiner* — Kyle Nottingham
(74) *Attorney, Agent, or Firm* — Dickinson Wright PLLC; Kristopher Lance Anderson

(57) ABSTRACT

Disclosed is a composition and method for a therapeutic treatment that is able to combat triple negative breast cancers (TNBCs). The class of urea compounds acts by blocking at inhibiting the mTOR signaling pathway, which, as a central regulator of mammalian metabolism and physi- (Continued)

ology that when inhibited leads to the induction of autophagocytosis. The disclosed compounds are further capable of reinitiating the p53 cycle as well as inhibition of the BNIP3/BNIP3L pathway. The disclosed compounds also shows the ability to cross the blood-brain-barrier where metastases can form. This new drug has the potential to be a powerful new treatment to combat invasive TNBCs.

2 Claims, 13 Drawing Sheets

(56) References Cited

FOREIGN PATENT DOCUMENTS

| | | |
|---|---|---|
| WO | 2019032924 A1 | 2/2019 |
| WO | 2020033909 A1 | 2/2020 |

OTHER PUBLICATIONS

Raju, B., et al., "Solution-phase combinatorial synthesis of ureas using nitrophenylcarbamates", Bioorganic & Medicinal Chemistry Letters, vol. 8, No. 21, Nov. 3, 1998, 3043-3048; 6 pages.

Temal, T. et al., "New potent calcimimetics: 1. Discovery of a series of novel trisubstituted ureas", Bioorganic & Medicinal Chemistry Letters, vol. 23, No. 8, Jan. 29, 2013, 2451-2454; 4 pages.

International Searching Authority, International Search Report and Written Opinion for PCT/US2019/046031; dated Oct. 11, 2019; 18 pages.

\* cited by examiner

SUBSTITUTED BISPHENYLALKYLUREA COMPOUNDS AND METHODS OF TREATING BREAST CANCER

CROSS-REFERENCE TO RELATED APPLICATIONS

The present application is a 35 U.S.C § 371 national application of PCT Application No. PCT/US19/46031, filed on Aug. 9, 2019, entitled "Substituted Bisphenylalkylurea Compounds And Methods Of Treating Breast Cancer", which claims priority to U.S. Provisional Patent Application No. 62/716,933 filed on Aug. 9, 2018, titled "Substituted Bisphenylalkylurea Compounds And Methods Of Treating Breast Cancer," and which patent applications are commonly owned by the owner of the present invention. These patent applications and their content are incorporated by reference in their entirety.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of therapeutic treatment. In particular, the present invention provides for a novel class of chemical compounds with anti-cancer properties. The disclosed compounds have potential to be used in patients with certain cancers.

STATEMENT OF FEDERALLY FUNDED RESEARCH

None.

BACKGROUND OF THE DISCLOSURE

Cancer can be defined as a group of diseases involving abnormal cell growth with the potential to invade or spread to other parts of the body. Besides skin cancer, breast cancer is the most commonly diagnosed cancer among American women, and roughly 15% of breast cancers classify as triple-negative breast cancer.

Triple-negative breast cancer (TNBC) is a breast cancer cell that does not express the genes for estrogen receptor, progesterone receptor, or HER-2. These cancers can be especially hard to treat since most hormone therapies target one of these receptors. Due to this, most TNBCs require a combination of different treatment methods that can be invasive and hard on the body. TNBC is one of the most aggressive types of breast cancer with higher rates of brain metastasis and low rate of survival. Currently there are a very few drugs for treating TNBC and even lesser number is capable to penetrate the blood-brain barrier (BBB) to reach metastasis. TNBC is an aggressive and heterogeneous subtype group of breast cancers clinically defined by the lack of estrogen and progesterone receptors, as well as the human epidermal growth factor receptor 2 (HER2).

SUMMARY OF THE DISCLOSURE

The present invention addresses failings in the art by providing compositions of substituted bisphenylalkylureas, and methods for a therapeutic treatment that is able to combat TNBC. 1-(5,5-bis(4-methoxyphenyl)pentyl)-3-(4-chloro-3-nitrophenyl)urea, has been shown to be effective in stopping the growth of TNBCs and their metastases. The compound is suggested to act by inhibiting the mTOR signaling pathway which leads to autophagocytosis in which the cell degrades itself through lysosomes; however they are not certain of this yet. The mechanistic target of rapamycin or mTOR is a central regulator of mammalian metabolism and physiology that when inhibited leads to the induction of autophagocytosis. The drug also shows the ability to cross the blood-brain-barrier (BBB) where metastases can form. This novel class of compounds has the potential to be a powerful new treatment to combat invasive TNBCs.

In one aspect, the present invention provides a compound of substituted bisphenylalkylureas, or a pharmaceutically acceptable salt thereof. In another aspect, the present invention provides a compound comprising Formula I (see FIG. 1). In another aspect, the present invention provides a compound comprising Formula II (see FIG. 2). In another aspect, the present invention provides a compound comprising Formula III (see FIG. 3). In another aspect, the present invention provides a compound comprising Formula IV (see FIG. 4). In another aspect, the present invention provides a compound comprising Formula V (see FIG. 5). In another aspect, the present invention provides a compound comprising Formula VI (see FIG. 6). In another aspect, the present invention provides a compound comprising Formula VII (see FIG. 7). In another aspect, the present invention provides a compound comprising Formula VIII (see FIG. 8). In another aspect, the present invention provides a compound comprising Formula IX (see FIG. 9). In another aspect, the present invention provides a compound comprising Formula X (see FIG. 10). In another aspect, the present invention provides a compound comprising Formula XI (see FIG. 11).

In another aspect the present invention provides a compound comprising the general formula XII (see FIG. 12).

In another aspect of the present invention, a method is provided for treating a disease in a patient comprising administering to the patient a compound which is a substituted bisphenylalkylurea, or a pharmaceutically acceptable salt thereof, or Formula I, Formula II, Formula III, Formula IV Formula V, Formula VI Formula VII, Formula VIII Formula IX, Formula X, or Formula XI, or pharmaceutically acceptable salts thereof. In another aspect, the said compound decreases neuroinflammation by acting on one or more of Alzheimer's disease, Parkinson's disease, traumatic brain injury, and brain tumors. In another aspect the compound decreases neuroinflammation by inhibiting H1 and H2 receptors.

In another aspect the compound comprises an aqueous solution and one or more pharmaceutically acceptable excipients, additives, carriers or adjuvants. In another aspect the compound further comprises one or more excipients, carriers, additives, adjuvants, or binders in a tablet or capsule.

In a particular aspect of the present invention, the general compound is presented of the formula:

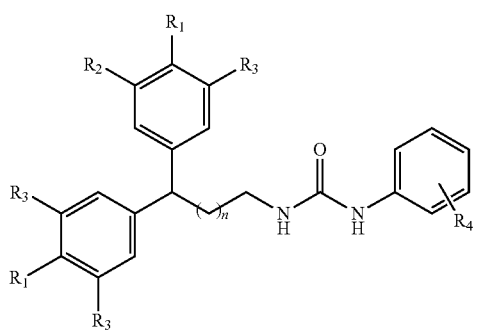

wherein:

R$_1$-R$_3$ are independently selected from a group consisting of: hydrogen, hydroxy, alkyloxy, halogen, alkyl ester, amine, alkylamine, dialkylamine, thio, thioalkyl, alkyl ethers;

R$_4$ is selected from a group consisting of: hydrogen, halogen, nitro, alkyl, aliphatic, cycloalkyl, trifluoroalkyl, substituted phenyl, carboxylic acid, alkyl ester of carboxylic acid, acetyl; and n=0 to 3, or a pharmaceutically acceptable salt thereof.

In one aspect, the compound is 1-(5,5-bis(4-methoxyphenyl)pentyl)-3-(4-chloro-3-nitrophenyl)urea, or a pharmaceutically acceptable salt thereof.

In one aspect, the compound has a formula:

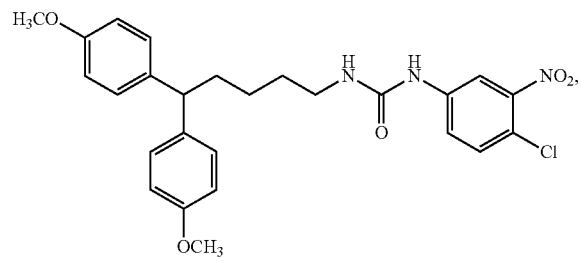 [SMILES: COc1ccc(C(CCCCNC(=O)Nc2ccc(Cl)c([N+](=O)[O-])c2)c2ccc(OC)cc2)cc1]

or a pharmaceutically acceptable salt thereof.

In another aspect, the present invention provides a compound of claim 1, wherein the formula selected from a group consisting of Formula I, Formula II, Formula III, Formula IV Formula V, Formula VI Formula VII, Formula VIII Formula IX, Formula X, and Formula XI.

In another aspect, a compound is presented having a formula selected from a group consisting of:

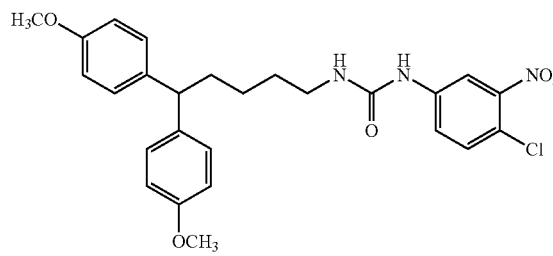

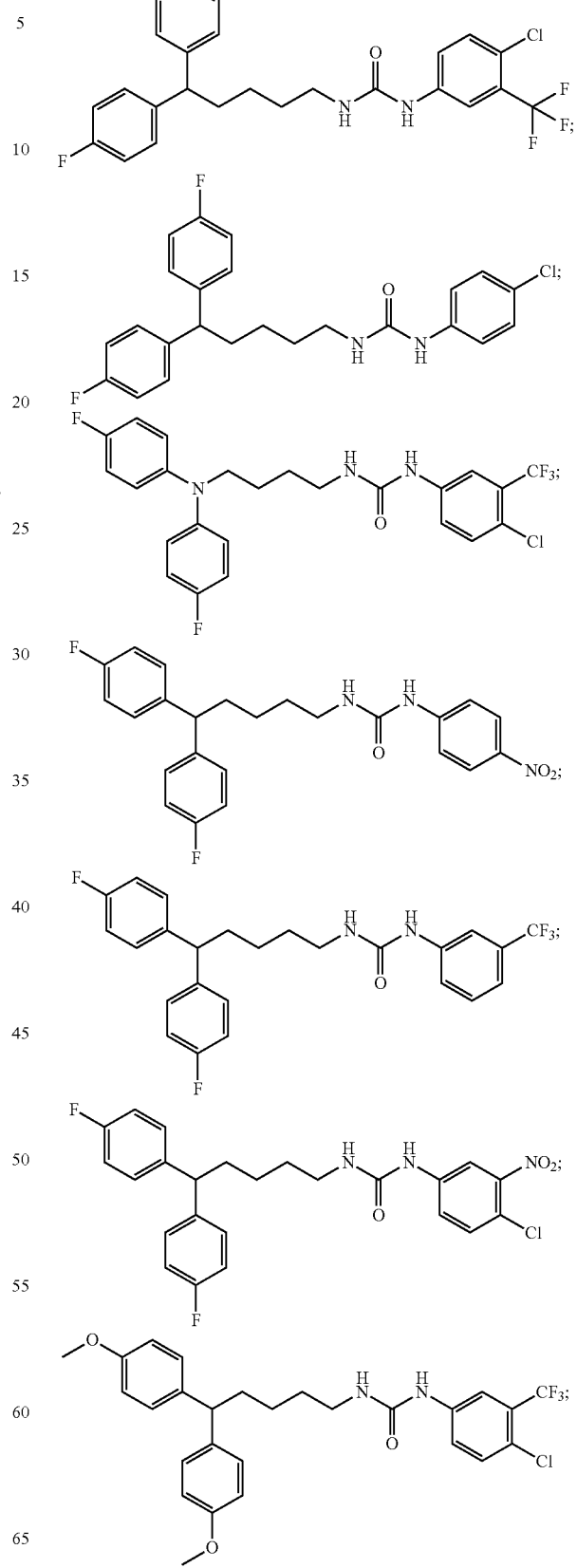

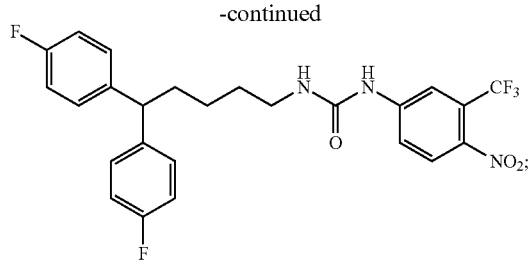

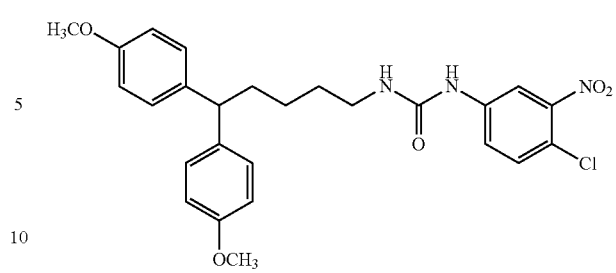

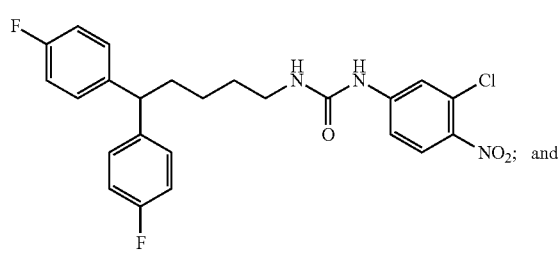

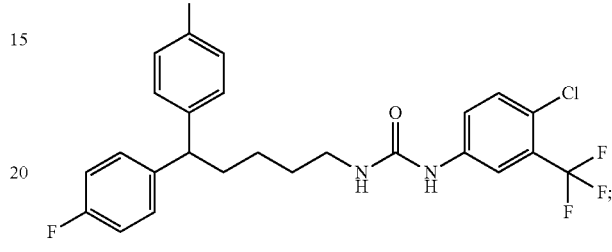

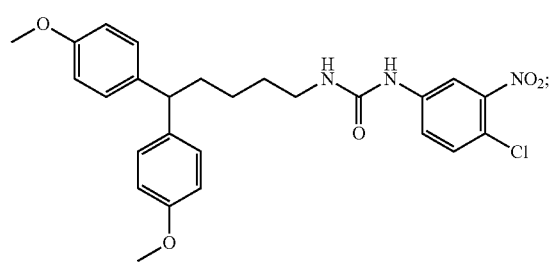

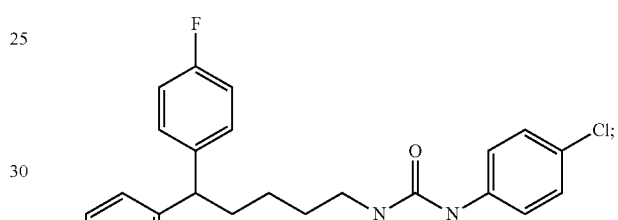

or a pharmaceutically acceptable salt thereof.

In one aspect, the pharmaceutical composition according further comprises one or more other anticancer agents. In another aspect, the pharmaceutical composition further comprises one or more other anticancer agents wherein said compound inhibits the mTOR signaling pathway. In another aspect, the composition further comprises one or more other anticancer agents wherein said compound reinitiates the p53 signaling pathway. In another aspect, the present invention provides compounds including one or more other anticancer agents wherein said compound inhibits of the BNIP3/BNIP3L pathway. In another aspect, the coumpounds are administered as a pharmaceutically acceptable salt thereof together with a pharmaceutically acceptable excipient. In another aspect the compounds further comprise one or more other anticancer agents.

It is another object of the present invention to provide a method for of treating triple-negative breast cancer in a mammal comprising the step of: administering to a patient a pharmaceutical acceptable amount of a compound being a bisphenylalkylurea compound. In another aspect, the compound selected from a group consisting of Formula I, Formula II, Formula III, Formula IV Formula V, Formula VI Formula VII, Formula VIII Formula IX, Formula X and Formula XI. In another aspect the compound is selected from a group consisting of:

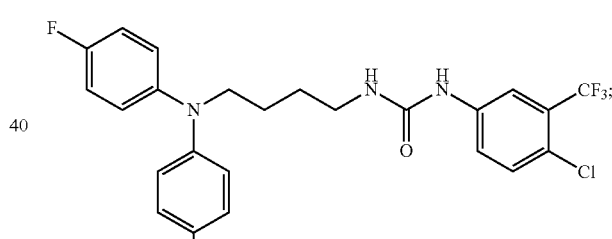

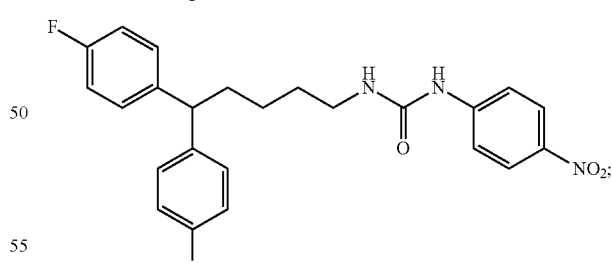

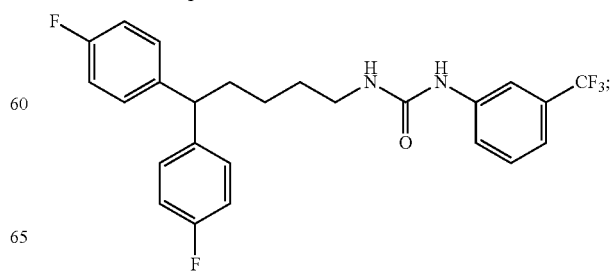

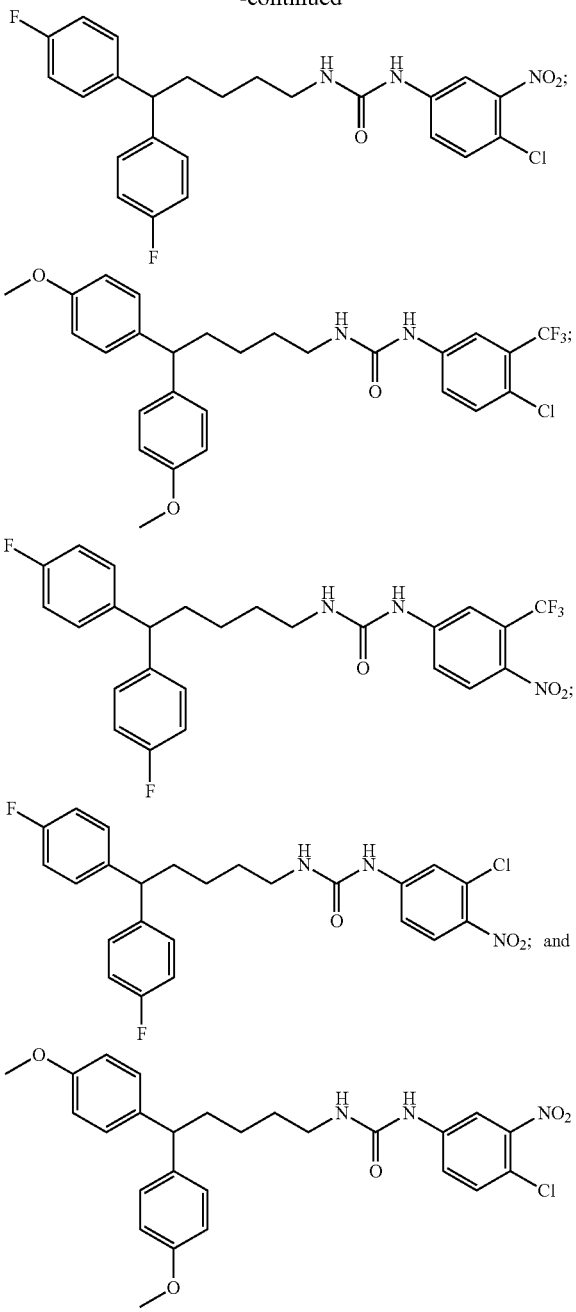

or a pharmaceutically acceptable salt thereof.

In one aspect the compound inhibits the mTOR signaling pathway. In another aspect the compound reinitiates the p53 signaling pathway. In another aspect the compound inhibits the BNIP3/BNIP3L pathway. The compound may further comprise an aqueous solution and one or more pharmaceutically acceptable excipients, additives, carriers or adjuvants. The compound further may further comprise one or more excipients, carriers, additives, adjuvants, or binders in a tablet or capsule.

In another aspect the compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF THE DISCLOSURE

Figure 1:
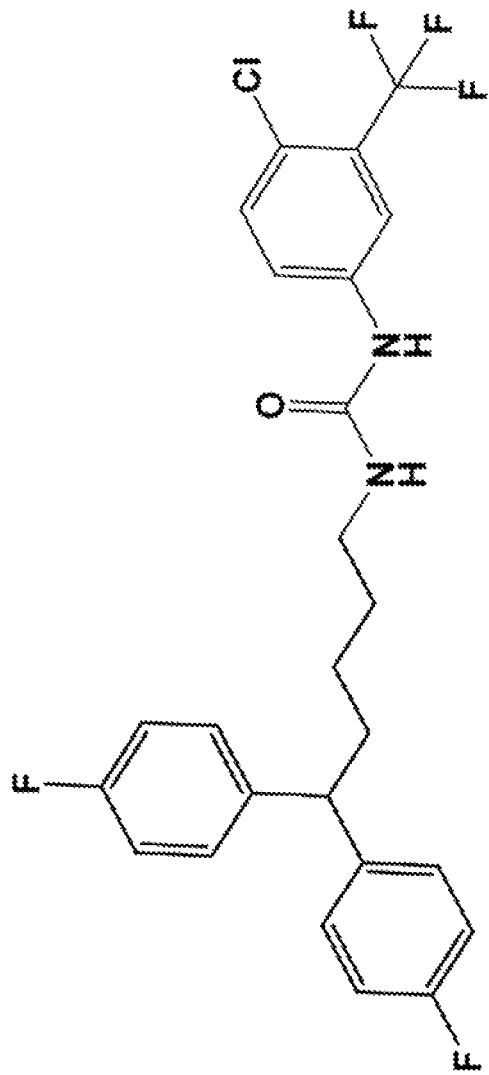
FIG. 1 depicts Formula I.

While the making and using of various embodiments of the present invention are discussed in detail below, it should be appreciated that the present invention provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present invention will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, or systems. Accordingly, embodiments may, for example, take the form of methods, compositions, compounds, materials, or any combination thereof. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The terms "subject", "individual", or "patient" are used interchangeably herein and refer to an animal preferably a warm-blooded animal such as a mammal. Mammal includes without limitation any members of the Mammalia. In general, the terms refer to a human. The terms also include domestic animals bred for food or as pets, including equines, bovines, sheep, poultry, fish, porcines, canines, felines, and zoo animals, goats, apes (e.g. gorilla or chimpanzee), and rodents such as rats and mice.

A compound of the Formula I, Formula II, Formula III, Formula IV Formula V, Formula VI Formula VII, Formula VIII Formula IX, Formula X, Formula XI, or Formula XII, can exist in unsolvated as well as solvated forms with pharmaceutically acceptable solvents such as water, ethanol, and the like. The solvated forms may be considered equivalent to the unsolvated forms for the purposes of the present invention.

"Therapeutically effective amount" relates to the amount or dose of an active compound of the Formula I, Formula II, Formula III, Formula IV Formula V, Formula VI Formula VII, Formula VIII Formula IX, Formula X, Formula XI, or Formula XII, or a composition comprising the same, that will lead to one or more desired effects, in particular, one or more therapeutic effects, more particularly beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

Figure 2:
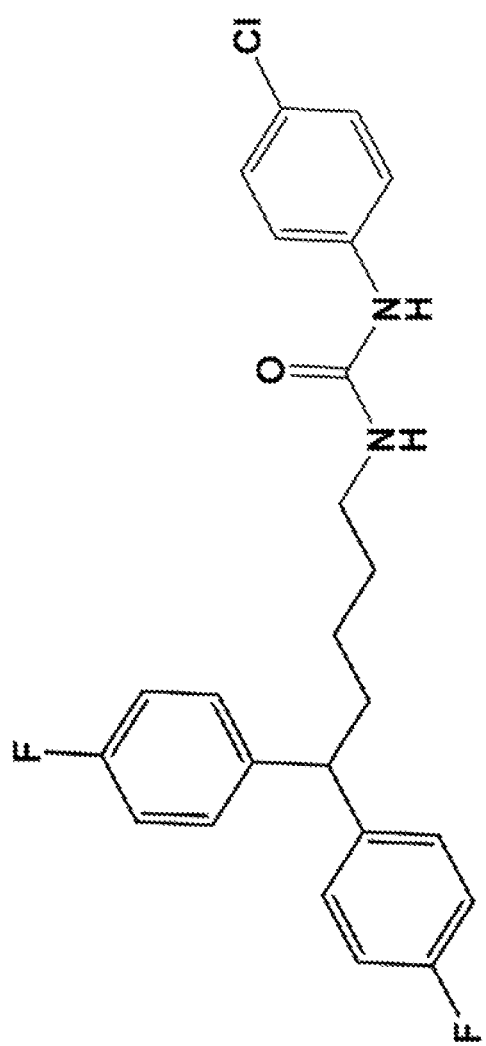
FIG. 2 depicts Formula II.
Figure 3:
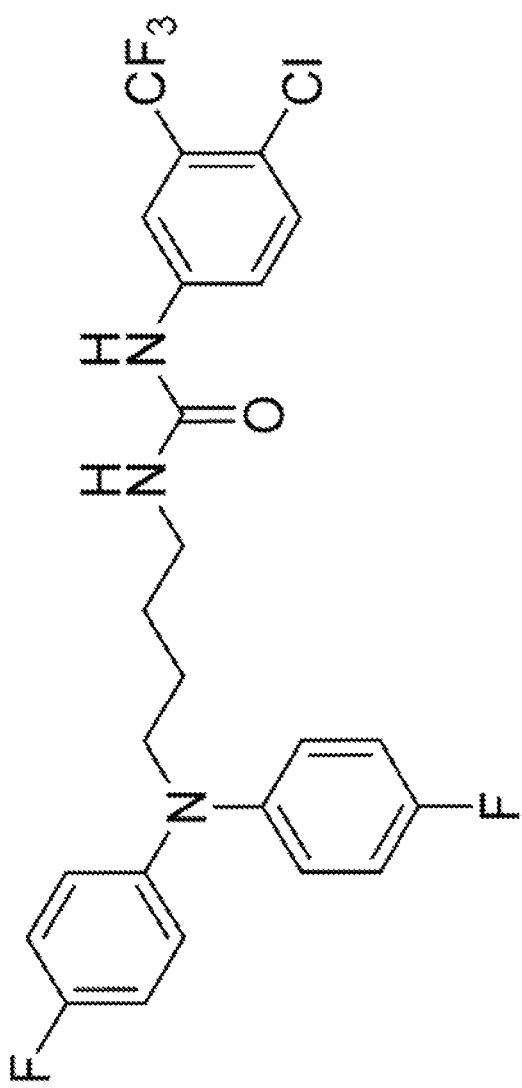
FIG. 3 depicts Formula III.
Figure 4:
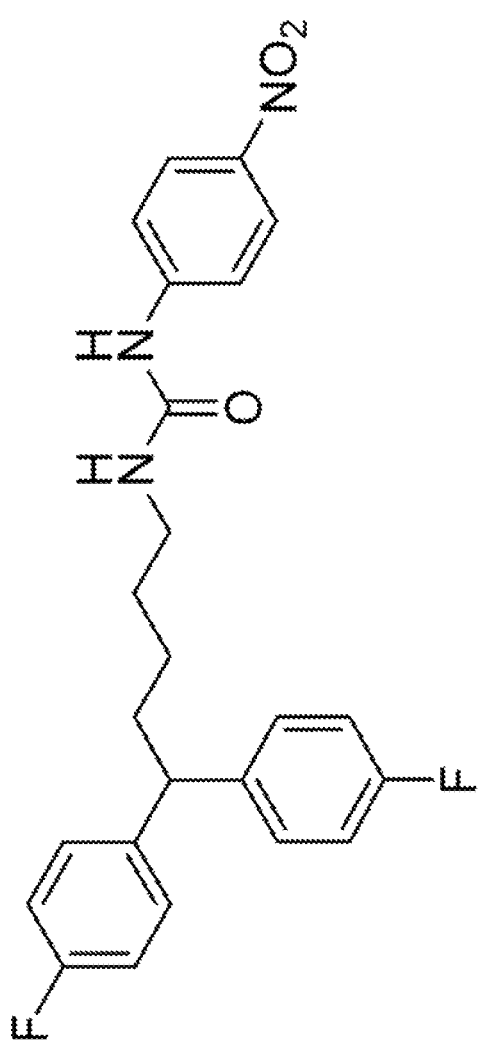
FIG. 4 depicts Formula IV.
Figure 5:
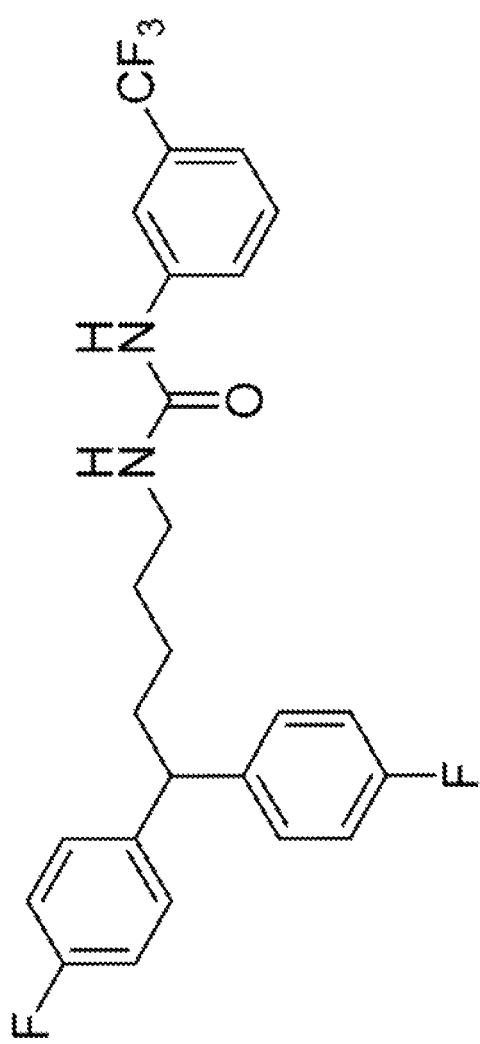
FIG. 5 depicts Formula V.
Figure 6:
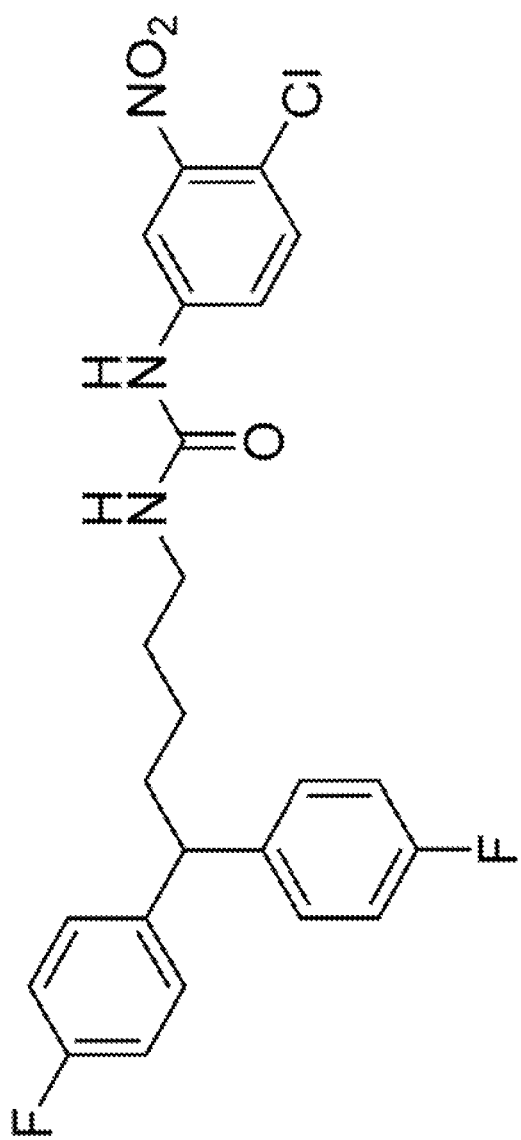
FIG. 6 depicts Formula VI.
Figure 7:
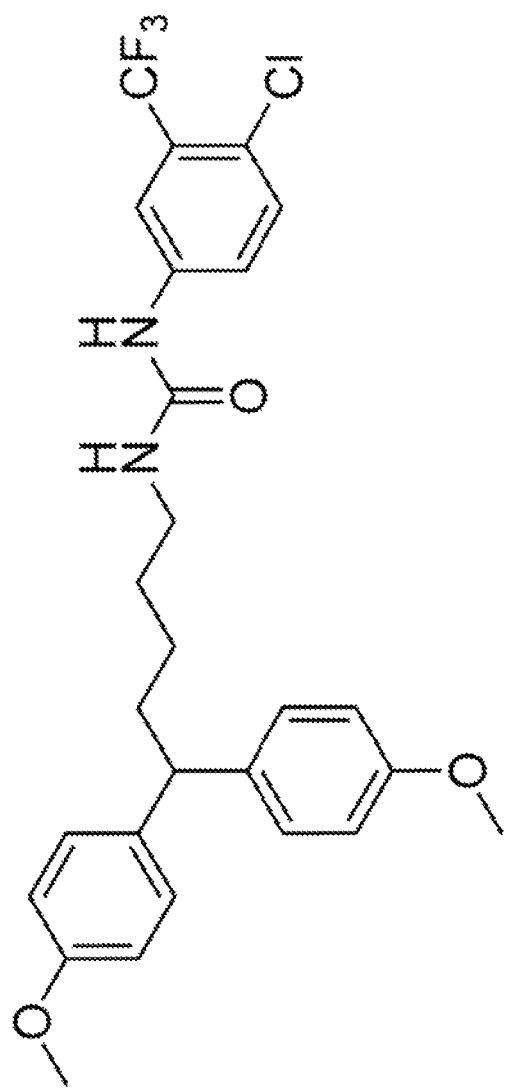
FIG. 7 depicts Formula VII.
Figure 8:
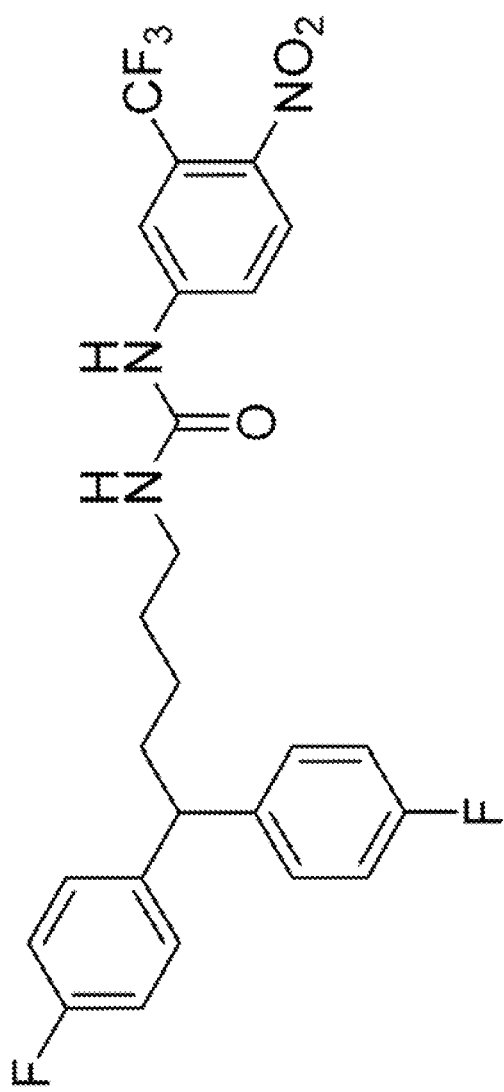
FIG. 8 depicts Formula VIII.
Figure 9:
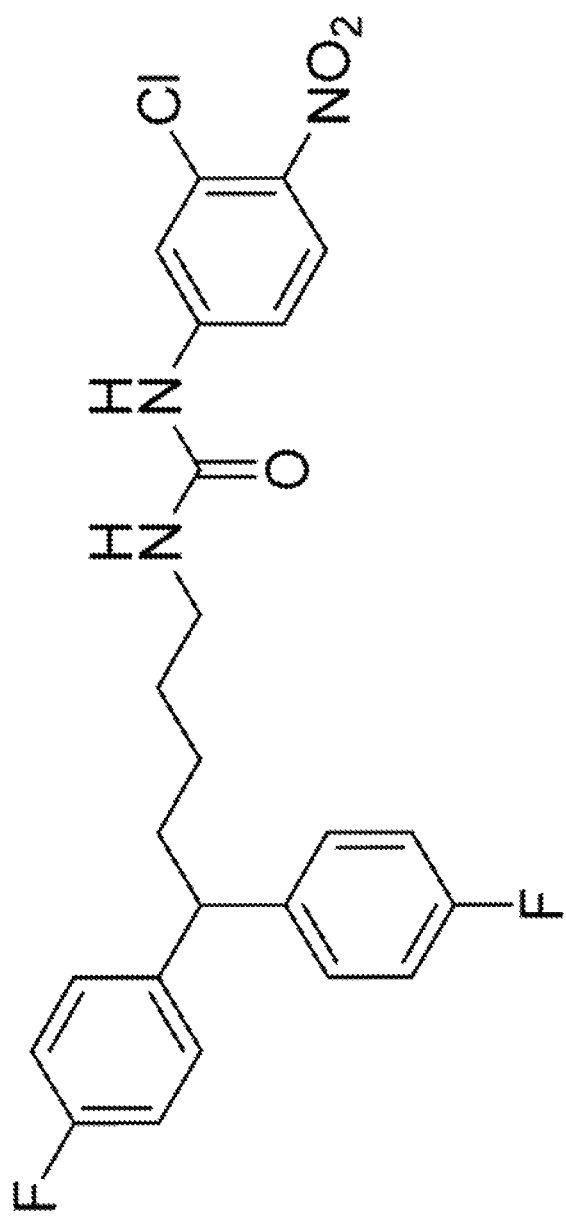
FIG. 9 depicts Formula IX.
Figure 10:
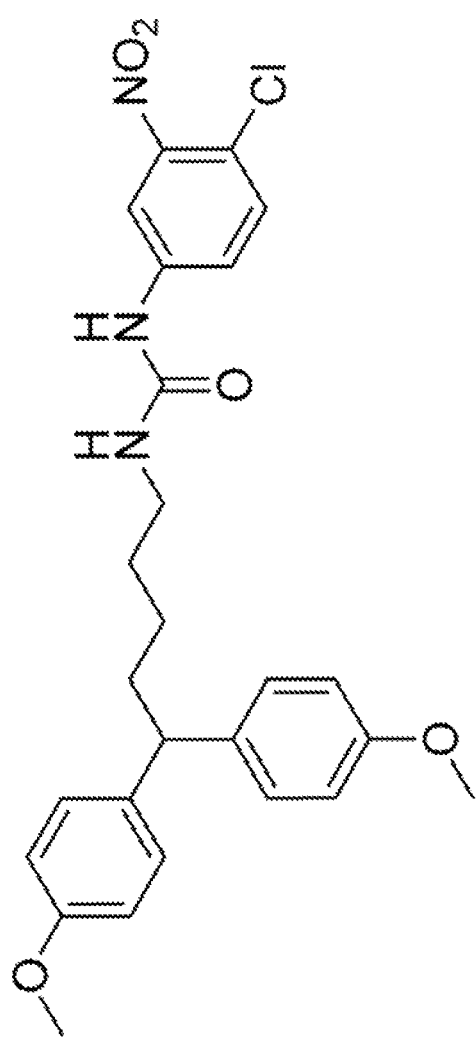
FIG. 10 depicts Formula X.
Figure 11:
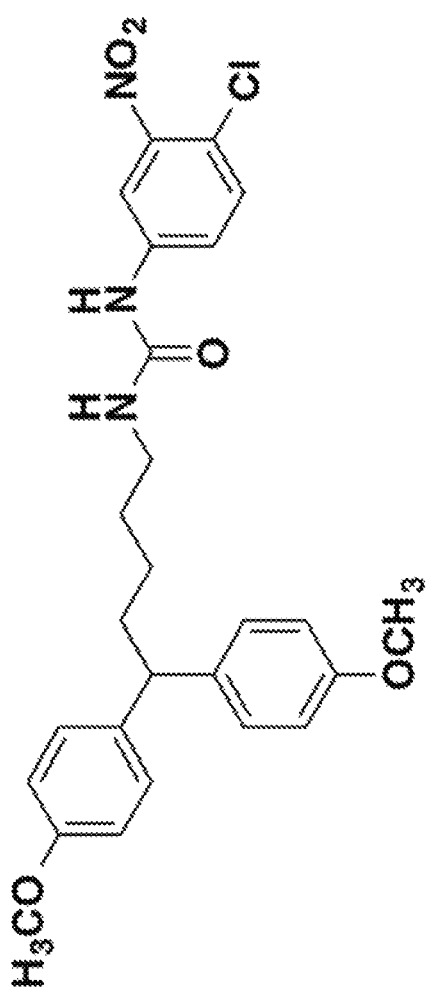
FIG. 11 depicts Formula XI.
Figure 12:
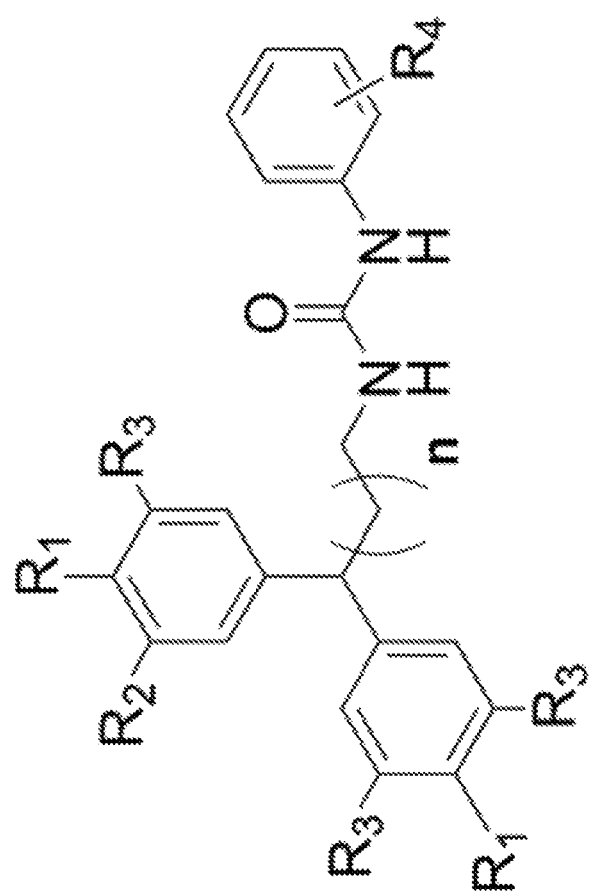
FIG. 12 depicts general compound Formula XII.

It is therefore an embodiment of the present invention to provide novel derivative compounds of urea for treating TNBC in a patient, wherein compounds of Formula I, Formula II, Formula III, Formula IV Formula V, Formula VI Formula VII, Formula VIII Formula IX, Formula X, Formula XI, or Formula XII, or pharmaceutically acceptable salts thereof, are presented. It is one embodiment of the present invention to provide a compound of Formula I (see FIG. 1). It is another embodiment of the present invention to provide a compound of Formula II (see FIG. 2). It is another embodiment of the present invention to provide a compound of Formula III (see FIG. 3). It is another embodiment of the present invention to provide a compound of Formula IV (see FIG. 4). It is another embodiment of the present invention to provide a compound of Formula V (see FIG. 5). It is another embodiment of the present invention to provide a compound of Formula VI (see FIG. 6). It is another embodiment of the present invention to provide a compound of Formula VII (see FIG. 7). It is another embodiment of the present invention to provide a compound of Formula VIII (see FIG. 8). It is another embodiment of the present invention to provide a compound of Formula IX (see FIG. 9). It is another embodiment of the present invention to provide a compound of Formula X (see FIG. 10). It is another embodiment of the present invention to provide a compound of Formula XI (see FIG. 11). It is another embodiment of the present invention to provide a compound of general Formula XII (see FIG. 12).

It is another embodiment of the present invention to provide a pharmaceutically acceptable compositions comprising compounds of Formulas I-XII, and a pharmaceutically acceptable carrier.

In another embodiment, the compounds, compositions, and methods disclosed herein therefore may be utilized to prevent and/or treat a disease involving neuroinflammation. mTOR (the mammalian or mechanistic target of rapamycin) is a protein kinase that forms two distinct types of multiprotein complex, termed mTOR complexes 1 and 2 (mTORC1 and mTORC2). Each plays key roles in cellular regulation. Given the many oncogenic pathways—and oncogenes or tumor suppressors—linked to mTOR signaling, this has resulted in much emphasis in targeting mTOR for cancer therapy. As noted, it is very common that cellular signaling pathways involving the mTOR complexes are abnormally upregulated in cancer. However, rapamycin properties are not entirely beneficial.

In an illustrative embodiment of the present invention, Formulas I-X, were evaluated for treatment of triple negative breast cancer (TNBC). Turning to Table 1, the half maximal inhibitory concentration (IC50) is a measure of the potency of a substance in inhibiting a specific biological or biochemical function.

This quantitative measure indicates how much of a particular drug or other substance (inhibitor) is needed to inhibit a given biological process (or component of a process, i.e. an enzyme, cell, cell receptor or microorganism) by half. The values are typically expressed as molar concentration.

TABLE 1

Inhibitory concentration 50 (IC50) wherein MCF7 = human breast adenocarcinoma cell line; and MDA MB 231 = human triple negative breast cancer cell line.

| Formula | MCF7 cell line 72 hrs | MDA MB 231 cell line 72 hrs |
|---|---|---|
| 1 | 7.07 | 7.1 |
| 2 | 17.31 | 16.39 |
| 3 | 8.93 | 7.64 |
| 4 | 18.03 | 24.11 |
| 5 | 14.69 | 11.30 |
| 6 | 9.0 | 8.8 |
| 7 | 8.4 | 9.7 |
| 8 | 4.3 | 4.5 |
| 9 | 14.6 | 19.6 |
| 10 | 9.1 | 13.6 |

In one embodiment, compound of the present invention Formulas I-X are shown Table 1 to show IC50 values suggesting micromolar values as an in vitro.

Figure 13:
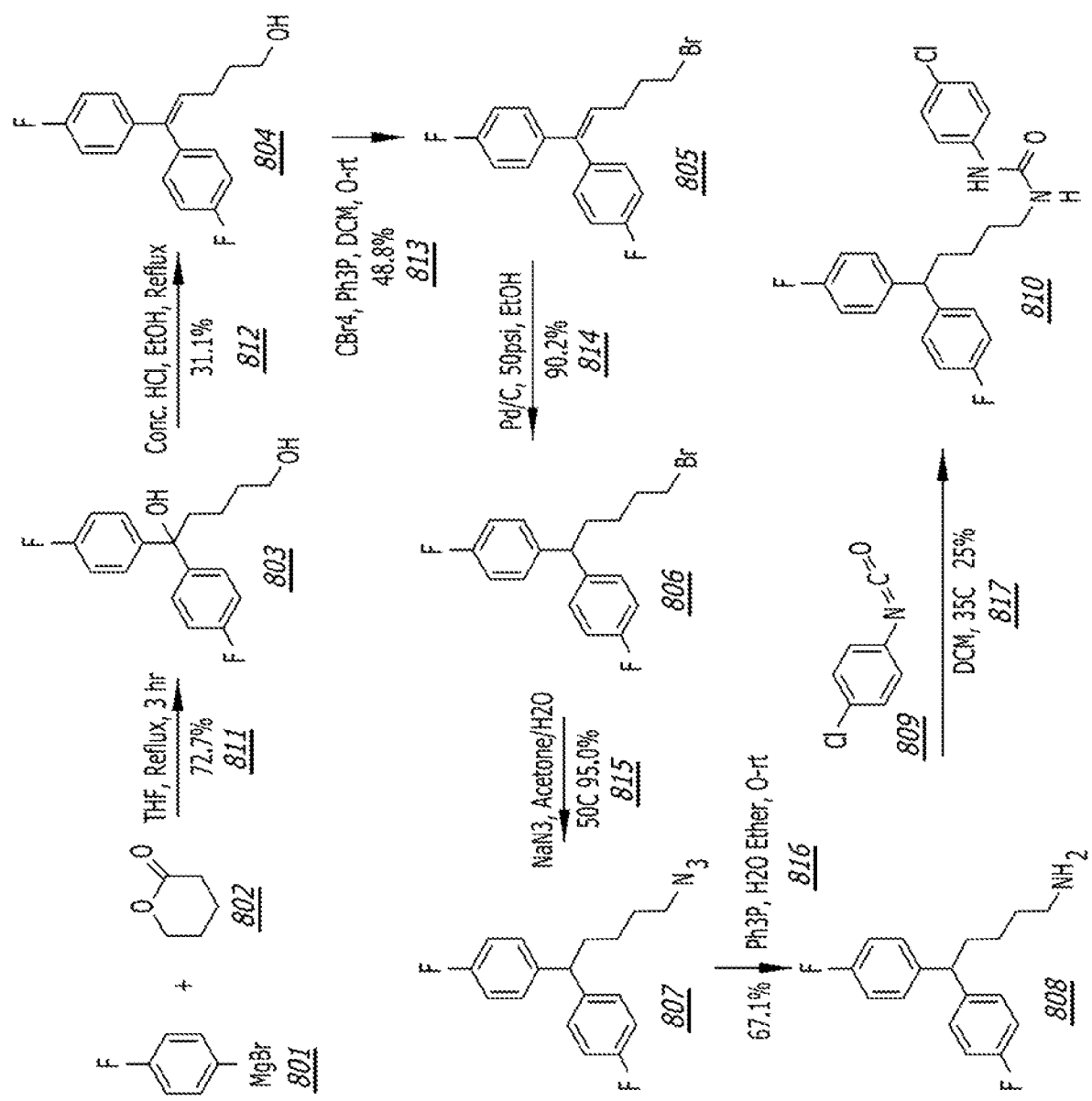
FIG. 13 is a schematic of a process to synthesize of an embodiment of the present invention.

FIG. 13 shows an example of a process for synthesizing 1-(5,5-bis(4-fluorophenyl)pentyl)-3-(4-chlorophenyl)urea (compound 810). In step 811, 2M 4-fluorophenyl magnesium bromide (compound 801) in ether (25 ml, 50 mmol) was taken in a dry two neck 100 ml round bottom flask under nitrogen environment. Delta valerolactone (compound 802) (2 g, 20 mmol) was dissolved in 20 ml THF dropwise and added to the reaction mixture. The reaction mixture was refluxed for 3 hours. Upon completion, the reaction was quenched with HCl (aq), followed by removal of THF using a rotary evaporator. The crude product was extracted using diethyl ether (3×15 ml). The combined organic portion was washed with brine solution, dried over anhydrous sodium sulfate, filtered and evaporated to dryness. The crude product was purified by chromatography using silica gel and hexane: ethyl acetate 30%-50%. Product (4.2 g, 72.7% yield) was obtained as a light yellow solid. 1H NMR (400 MHz, CHLOROFORM-d) δ ppm 1.35 (br d, J=7.58 Hz, 2H) 1.46-1.71 (m, 2H) 2.20-2.38 (m, 2H) 3.62 (t, J=6.36 Hz, 2H) 4.12 (t, J=7.09 Hz, 1H) 6.95-7.02 (m, 4H) 7.31-7.39 (m, 4H). This product was 1,1-bis(4-fluorophenyl)pentane-1,5-diol (compound 803).

In step 812, a reaction mixture containing, 1-bis(4-fluorophenyl)pentane-1,5-diol (compound 803) (4.2 g, 14.5 mmol) and HCl (conc) (17 mL) in ethanol (200 mL) was refluxed for 12 hours. Upon completion, the reaction was neutralized using with NaHCO$_3$ and dried with Na$_2$SO$_4$. Filtration, evaporation in vacuo, and purification by flash chromatography (PE:EtOAc=3:1–1:1) afforded desired product in the form of light yellow liquid (1.25 g, 31.1%). 1H NMR (400 MHz, CHLOROFORM-d) δ ppm –0.02–0.01 (m, 1H) 0.01-0.02 (m, 1H) 1.70 (dd, J=7.83, 6.85 Hz, 2H) 2.18 (d, J=7.34 Hz, 2H) 3.63 (t, J=6.48 Hz, 2H) 6.02 (t, J=7.45 Hz, 1H) 6.95 (t, J=8.10 Hz, 2H) 7.04-7.18 (m, 6H). This product was 5,5-bis(4-fluorophenyl)pent-4-en-1-ol (compiund 804).

In step 813, Ph$_3$P (2.26 g, 8.64 mmol) was added to a solution of 5,5-bis(4-fluorophenyl)pent-4-en-1-ol (compiund 804) (1.25 g, 4.55 mmol) in CBr$_4$ (1.8 g, 5.46 mmol) in dry CH$_2$Cl$_2$ (45 mL) at 0° C. The reaction mixture was allowed to warm to room temperature slowly. After stirring for 4 to 5 hours, the reaction was completed. The reaction mixture was filtrated, and washed using petroleum ether. Organic solvents were removed using a rotary evaporator, and the final product was purified using flash chromatography (EA:Hex=20:1–10:1) to afford 0.76 g (48.9%) of a liquid. $^1$HNMR (400 MHz, CHLOROFORM-d) δ ppm 1.95-2.05 (m, 2H) 2.25 (q, J=7.34 Hz, 2H) 3.38 (t, J=6.72 Hz, 2H) 5.97 (t, 1H) 6.95 (t, J=8.11 Hz, 2H) 7.04-7.19 (m, 6H). This product was 4,4'-bis(5-bromopent-1-ene-1,1diyl) bis (flurobenzene) (compound 805).

In step 814, a solution of 4,4'-bis(5-bromopent-1-ene-1,1diyl)bis (flurobenzene) (compound 805) (0.760 g) and Pd—C(70 mg, 10%) in ethanol (30 mL) was stirred under hydrogen atmosphere (50 psi) overnight at room temperature. Upon reaction completion, the mixture was filtered through celite and concentrated in vacuo. The crude product was purified by flash chromatography (Hex:EA=30:1-115:1) to yield 0.684 g (90.1%) of a final product as a liquid. $^1$H NMR (400 MHz, CHLOROFORM-d) δ ppm 1.39 (br d, J=7.34 Hz, 2H) 1.82-1.95 (m, 2H) 2.00 (br d, J=7.83 Hz, 2H) 3.36 (t, J=6.72 Hz, 2H) 3.86 (s, 1H) 6.97 (br t, J=8.68 Hz, 4H) 7.15 (br dd, J=8.19, 5.50 Hz, 4H). This product was 4,4'-(5-bromopentane-1,1-diyl)bis(fluorobenzene) (compound 806).

In step 815, NaN$_3$ (0.150 g, 1.87 mmol, 5 equiv.) was added to a solution of 4,4'-(5-bromopentane-1,1-diyl)bis (fluorobenzene) (compound 806) (0.120 g, 0.37 mmol, 1 equiv.) in 2 ml of acetone. Water was added dropwise with shaking until NaN$_3$ dissolved entirely and made a clear solution. Then the reaction mixture was kept stirring at 45° C. for 24 hours. The reaction was followed by TLC and reaction solvent was removed upon reaction completion. Resulted residue was dissolved in water and extracted using chloroform to obtain 0.101 g (95.1%) of the final product. $^1$H NMR (400 MHz, CHLOROFORM-d) δ ppm 1.31 (m, 2H) 1.57-1.67 (m, 2H) 2.01 (dd, J=7.83 Hz, 2H) 3.23 (t, J=6.97 Hz, 2H) 3.86 (t, 1H) 6.94-7.01 (m, 4H) 7.12-7.18 (m, 4H). This product was 4,4'-(5-azidopentane-1,1-diyl)bis (fluorobenzene) (compound 807).

In step 816, Ph$_3$P (0.130 g, 0.498 mmol, 1.5 equiv.) was added to a solution of compound 7 (0.100 g, 0.332 mmol, 1 eq) in dry di-ethyl-ether (2.5 ml) at 0□C and stirred for 3 hours 0° C. Water (0.05 ml) was added to the reaction vessel and stirred overnight at room temperature. Upon full consumption of azide, the reaction solvent was removed, and formed residue was purified using flash chromatography (0-10% MeOH in DCM+ 0.1% TEA) to obtain 0.061 g (67%) of the desired product. $^1$H NMR (400 MHz, CHLOROFORM-d) δ ppm 1.26 (m, 21H) 1.37-1.60 (m, 2H) 1.98 (q, 2H)2.56-2.78 (t, 2H)3.85 (t, 1H)6.95 (m, 4H)7.05-7.26 (m, 4H). This product was 5,5-bis(4-fluorophenyl)pentan-1-amine (compound 808).

In step 817, 1-chloro-4-isocyanatobenzene (compound 809) (0.016 g, 0.11 mmol, 1 equiv.) was added to the solution of 5,5-bis(4-fluorophenyl)pentan-1-amine (compound 808) (0.030 g, 0.11 mmol, 1 equiv.) in DCM (4 ml) and stirred under an inert environment at 35° C. for 4 hours. The reaction was monitored using TLC (5% EA in DCM, Rf=0.3). Upon completion, the reaction solvent was removed in vacuum and the final product was obtained upon crystallization in the ether (0.012 g (25%), white powder). $^1$H NMR (400 MHz, CHLOROFORM-d) δ ppm 1.13-1.37 (m, 2H) 1.42-1.59 (m, 2H) 1.97 (br d, J=7.83 Hz, 2H) 3.16 (br d, J=6.11 Hz, 2H) 3.82 (s, 1H) 4.77 (s, 1H) 6.52 (s, 1H) 6.86-7.04 (m, 4H) 7.07-7.28 (m, 8H) 13C NMR (101 MHz, CHLOROFORM-d) δ ppm 25.16 (s, 1 C) 29.96 (s, 1 C) 35.47 (s, 1 C) 40.16 (s, 1 C) 49.66 (s, 1 C) 115.20 (s, 1 C) 115.40 (s, 1C) 121.87 (s, 1 C) 128.77 (s, 1 C) 129.02 (s, 1 C) 129.09 (s, 1 C) 129.23 (s, 1 C) 137.15 (s, 1 C) 140.39 (s, 1 C) 140.42 (s, 1 C) 155.41 (s, 1 C) 160.12 (s, 1 C) 162.55 (s, 1 C). This final product was 1-(5,5-bis(4-fluorophenyl)pentyl)-3-(4-chlorophenyl)urea (compound 810).

It is another embodiment of the present invention relates to compounds of general Formula XII:

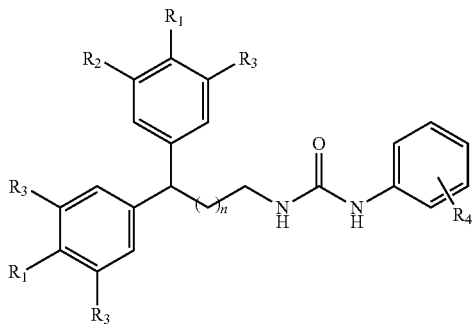

wherein:
R1=hydrogen, hydroxy, alkyloxy, halogen, alkyl ester, amine, alkylamine, dialkylamine, thio, thioalkyl, alkyl ethers;
R2=hydrogen, hydroxy, alkyloxy, halogen, alkyl ester, amine, alkylamine, dialkylamine, thio, thioalkyl, alkyl ethers;
R3=hydrogen, hydroxy, alkyloxy, halogen, alkyl ester, amine, alkylamine, dialkylamine, thio, thioalkyl, alkyl ethers;
R4=hydrogen, halogen, nitro, alkyl, aliphatic, cycloalkyl, trifluoroalkyl, substituted phenyl, carboxylic acid, alkyl ester of carboxylic acid, acetyl; and
n=0 to 3.

As used herein, the term "compound" is intended to refer to a chemical entity, whether in the solid, liquid or gaseous phase, and whether in a crude mixture or purified and isolated.

As used herein the term "alkyl" includes both straight chain and branched alkyl groups having from 1 to 8 carbon atoms, e.g. methyl, ethyl propyl, isopropyl, butyl, isobutyl, tert-butyl, pentyl, hexyl etc. and the term "lower alkyl" is similarly used for groups having from 1 to 4 carbon atoms.

The term "aryl" is used to include groups having from 6 to 10 carbon atoms, e.g. phenyl, naphthyl etc.

The term "aralkyl" is used as a conjunction of the terms alkyl and aryl as given above.

The compositions includes those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier or both, and then, if necessary, shaping the product into desired formulations.

Preferably, for purposes of cancer therapy, a compound of Formulas I-XI or general Formula XII is administered to the subject in an amount sufficient to either reinitiate the p53 pathway or inhibit the BNIP3/BNIP3L pathway, or combinations thereof, thereby inhibiting angiogenesis. However, the therapeutically effective dosage of any specific compound will vary somewhat from compound to compound, patient to patient, and will depend upon the condition of the patient and the route of delivery. When administered conjointly with other pharmaceutically active agents, even less of the compounds of Formulas I-XI or general Formula XII may be therapeutically effective. The compound of Formulas I-XI or general Formula XII may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

The identified targets further include BNIP3 and p53-related pathways that are well established targets in the cancer treatment.

The p53 gene is mutated in over 50 different types of human cancers, including familial and spontaneous cancers, and is believed to be the most commonly mutated gene in human cancer. Greater than 90% of mutations in the p53 gene are missense mutations that alter a single amino acid that inactivates p53 function. Aberrant forms of human p53 are associated with poor prognosis, more aggressive tumors, metastasis, and short survival rates. In response to these signals, p53 protein levels are greatly increased with the result that the accumulated p53 activates cell cycle arrest or apoptosis depending on the nature and strength of these signals. Indeed, literature supports a key role for p53 as a tumor suppressor. It is therefore another embodiment of the present invention to reactivate the p53 pathway and induce apoptosis. Inactivation of the p53 pathway occurs in the majority of human cancers and often leads to resistance to therapy and poor survival. The determination of p53 status in clinical studies would strongly contribute to a better management of cancer and supports the rationale for clinical trials with p53-based therapy.

Overexpression of mutated p53 with reduced or abolished function is often connected to resistance to standard medications, including cisplatin, alkylating agents (temozolomide), anthracyclines, (doxorubicin), antimetabolites (gemcitabine), antiestrogens (tamoxifen) and EGFR-inhibitors (cetuximab). In the future, combination therapies consisting of standard cytotoxic drugs and novel small molecules targeting p53 and MDM2 may be the key to fight cancer. Overcoming resistance to classical anticancer drugs by exploitation of synergistic effects of novel small molecules bears a huge potential to substantially improve the outcome of cancer chemotherapy.

In another embodiment, the present invention provides inhibition of the BNIP3/BNIP3L pathway. A great number of studies have demonstrated that mitophagy can be inhibited through genetically or pharmacologically targeting different stages of the autophagic/mitophagic process, such as silencing of autophagic/mitophagic genes (e.g. autophagy-related 5 (ATG5), Parkin, PINK1, BNIP3 and BNIP3L), blocking the formation of autophagosomes by phosphoinositide 3-kinase (PI3K) inhibitors (e.g. 3-methyladenine and LY294002), and inhibiting the fusion of autophagosomes with lysosomes or the degradation capacity of autophagolysosomes (e.g. chloroquine, bafilomycin A1, leupeptin and liensinine).

It is another embodiment of the present invention to provide one of Formulas I-XI comprising an aqueous solution and one or more pharmaceutically acceptable excipients, additives, carriers or adjuvants. Formulas I-XI may further comprise one or more excipients, carriers, additives, adjuvants, or binders in a tablet or capsule. Formulas I-XI may further be administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

The compounds of the present invention are capable of treatment in a manner selective to CNS activity and does not manipulate the activity of other CNS receptors, as other CNS drugs have a tendency to do. Therefore, the compounds of the present invention have substantially reduced toxicity profiles (i.e. depression, headache, suicidal thoughts, and the like). The compounds are further active as low nanomolar ranges due to its potency.

Those skilled in the art will recognize that the methods and compositions of the present invention may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present invention covers conventionally known manners for carrying out the described features as well as those variations and modifications that may be made to the processes, composition, or compounds described herein as would be understood by those skilled in the art now and hereafter.

While various embodiments have been described for purposes of this disclosure, such embodiments should not be deemed to limit the teaching of this disclosure to those embodiments. Various changes and modifications may be made to the elements and operations described above to obtain a result that remains within the scope of the compositions and methods described in this disclosure.

What is claimed is:

1. A compound having a formula:

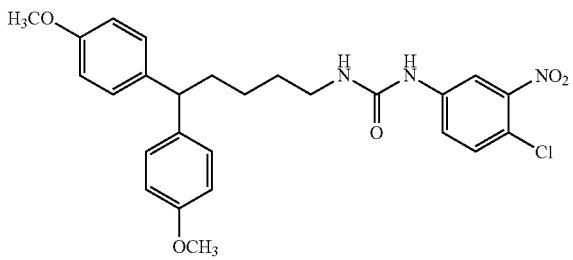 [SMILES: COc1ccc(C(CCCCNC(=O)Nc2ccc(Cl)c([N+](=O)[O-])c2)c2ccc(OC)cc2)cc1]

or a pharmaceutically acceptable salt thereof.

2. A compound having a formula selected from a group consisting of:

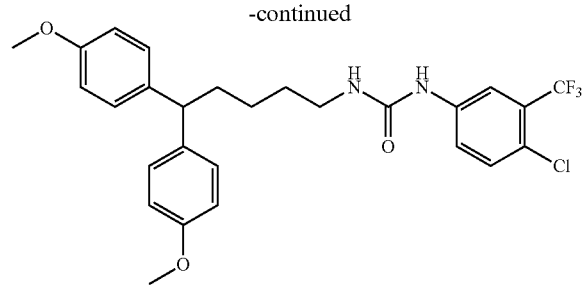
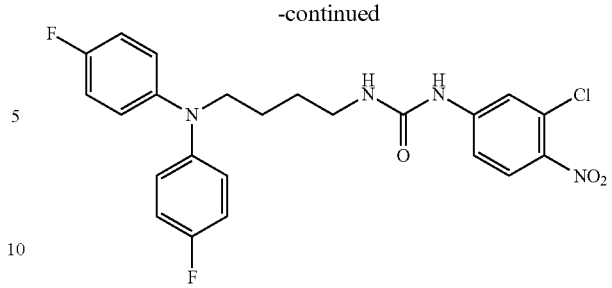
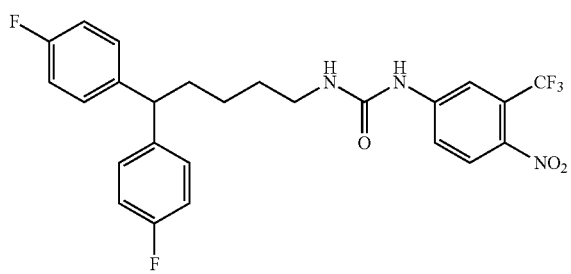
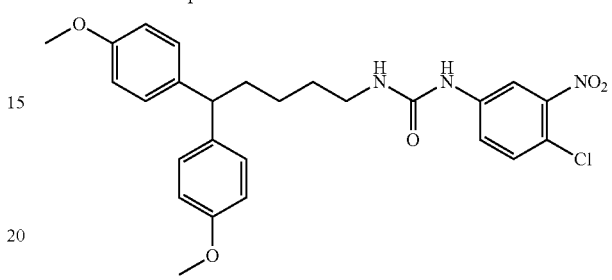
or a pharmaceutically acceptable salt thereof.
* * * * *